United States Patent [19]

Oe et al.

[11] 4,085,111
[45] Apr. 18, 1978

[54] 1H-TETRAZOLE DERIVATIVES

[75] Inventors: Takanori Oe, Nakatsu; Mineo Tsuruda, Shiidamachi, both of Japan

[73] Assignee: Yoshitomi Pharmaceutical Industries, Ltd., Osaka, Japan

[21] Appl. No.: 579,173

[22] Filed: May 20, 1975

[30] Foreign Application Priority Data

May 28, 1974 Japan .................................. 49-60632

[51] Int. Cl.$^2$ ................. C07D 401/14; A61K 31/535; A61K 31/495; A61K 31/435
[52] U.S. Cl. ........................ 260/296 H; 260/268 TR; 260/293.58; 424/248.56; 424/250; 424/256; 544/126
[58] Field of Search ............................. 424/269, 296; 260/308 D, 296 T, 296 H

[56] References Cited

U.S. PATENT DOCUMENTS

| | | | |
|---|---|---|---|
| 2,977,372 | 3/1961 | Finnegan et al. | 260/308 D |
| 3,536,715 | 10/1970 | Hayad et al. | 260/308 D |
| 3,755,319 | 8/1973 | Bays | 260/308 D |
| 3,931,199 | 1/1976 | Nakanishi et al. | 260/296 T |
| 3,939,173 | 2/1976 | Hodson et al. | 260/308 D |

FOREIGN PATENT DOCUMENTS 1,362,782   8/1974   United Kingdom ............ 260/308 D Primary Examiner—Frederick E. Waddell
Attorney, Agent, or Firm—Sughrue, Rothwell, Mion, Zinn and Macpeak

[57] ABSTRACT

1H-Tetrazole derivatives of the formula:

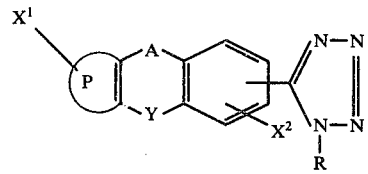

and pharmaceutically acceptable salts thereof, wherein the ring P is pyridine ring; A is carbonyl, methylene or $C_{2-4}$ alkylidene; Y is oxygen, sulfur or —N(R$^1$)— wherein R$^1$ is hydrogen or $C_{1-4}$ alkyl; each of $X^1$ and $X^2$ is hydrogen, halogen, $C_{1-4}$ alkyl, $C_{1-4}$ alkoxy, phenyl or substituted phenyl, any substitutent on the phenyl being halogen, $C_{1-4}$ alkyl, $C_{1-4}$ alkoxy or trifluoromethy; and R is hydrogen, $C_{1-4}$ alkyl, $C_{2-4}$ alkenyl, $C_{2-4}$ alkynyl, hydroxy-$C_{1-4}$ alkyl, $C_{1-4}$ alkoxy-$C_{1-4}$ alkyl, carboxy-$C_{1-4}$ alkyl, $C_{1-4}$ alkoxycarbonyl-$C_{1-4}$ alkyl or substituted or unsubstituted amino-$C_{1-4}$ alkyl, any substituted amino being $C_{1-4}$ alkyl- or di-$C_{1-4}$ alkyl-amino, piperidino, 1-pyrrolidinyl, morpholino, 1-piperazinyl and 4-$C_{1-4}$alkyl-1-piperazinyl; are useful as antiallergic agents.

2 Claims, No Drawings

1H-TETRAZOLE DERIVATIVES

This invention relates to novel and therapeutically valuable compounds of the formula:

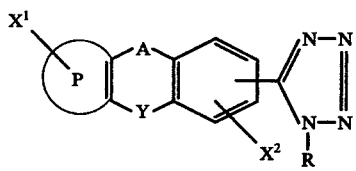

and pharmaceutically acceptable salts thereof, wherein the ring P represents a pyridine ring;

A represents a carbonyl group, a methylene group or as alkylidene group having 2 to 4 carbon atoms;

Y represents an oxygen atom, a sulfur atom or the group —N($R^1$)— wherein $R^1$ is a hydrogen atom or an alkyl group having 1 to 4 carbon atoms;

each of $X^1$ and $X^2$ represents a hydrogen atom, a halogen atom, an alkyl group having 1 to 4 carbon atoms, an alkoxy group having 1 to 4 carbon atoms, a phenyl group or a substituted phenyl group, any substituent on the phenyl group being a halogen atom, an alkyl group having 1 to 4 carbon atoms, an alkoxy group having 1 to 4 carbon atoms or a trifluoromethyl group; and R represents a hydrogen atom, an alkyl group having 1 to 4 carbon atoms, an alkenyl group having 2 to 4 carbon atoms, an alkynyl group having 2 to 4 carbon atoms, a hydroxyalkyl group in which the alkyl moiety has 1 to 4 carbon atoms, an alkoxyalkyl group in which each of alkoxy and alkyl moieties has 1 to 4 carbon atoms, a carboxyalkyl group in which the alkyl moiety has 1 to 4 carbon atoms, an alkoxycarbonylalkyl group in which each of alkyl and alkoxy moieties has 1 to 4 carbon atoms or a substituted or unsubstituted amino-alkyl group in which the alkyl moiety has 1 to 4 carbon atoms (the substituted amino group being for example alkyl- or dialkyl-amino in which each of alkyl moieties has 1 to 4 carbon atoms, piperidino, 1-pyrrolidinyl, morpholino, 1-piperazinyl or 4-alkyl-1-piperazinyl in which the alkyl moiety has 1 to 4 carbon atoms).

Examples of the groups mentioned above are: the alkyl group may be methyl, ethyl, propyl, isopropyl or butyl; the alkenyl group may be vinyl, allyl, isopropenyl or 2-butenyl; the alkynyl group may be ethynyl, 2-propynyl or 2-butynyl; the alkoxy group may be methoxy, ethoxy, propoxy, isopropoxy or butoxy; the alkylidene group may be ethylidene, propylidene, isopropylidene or butylidene; and the halogen atom may be F, Cl or Br.

The ring system:

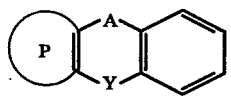

in the above formula [I] and in other formulae shown hereinafter represents any of the following structures (1) to (4).

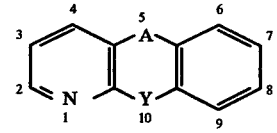

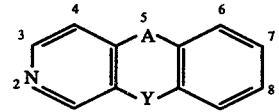

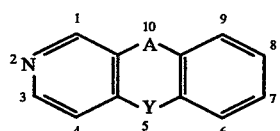

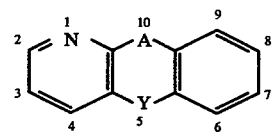

The compounds of formula [I] can be produced, for example, by the following methods suitably selected depending on the kind of the objective compounds [I]:

(i) By reacting a compound of the formula:

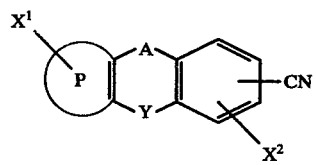

wherein each symbol is as defined above, with hydrazoic acid or an azide.

The aforesaid hydrazoic acid or azide is used in an amount not less than equimolar to the compound of formula [II]. An inorganic azide such as sodium azide, lithium azide, aluminum azide or ammonium azide is preferably used, though an organic azide such as trimethylammonium azide, morpholinium azide or piperidinium azide can be used.

The reaction is usually carried out in an anhydrous solvent (e.g. dimethylformamide, dimethyl sulfoxide, hexamethylphosphoramide, diethylene glycol monomethyl ether, tetrahydrofuran or n-butanol) in the presence of a catalyst such as boron trifluoride etherate, tetraalkylammonium chloride, aniline hydrochloride, ammonium chloride or lithium chloride at a temperature between 10° C and 200° C, preferably between 100° C and 140° C, for 5 to 24 hours.

The reaction (i) gives compounds of formula [I] wherein R is a hydrogen atom.

(ii) By subjecting a compound of the formula:

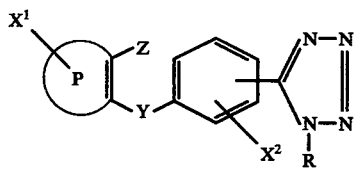

to intramolecular condensation, wherein Z is a carboxyl group or a functional derivative thereof (e.g. acid halide such as acid chloride or lower alkyl ester such as methyl ester or ethyl ester), and other symbols are as defined above.

The condensation is usually carried out in the presence of a condensing agent (e.g. sulfuric acid, polyphosphoric acid, phosphoric anhydride, phosphorus oxychloride, phosphorus pentachloride, aluminum chloride, zinc chloride or tin tetrachloride), if necessary, in an inert solvent (e.g. carbon disulfide, nitrobenzene, tetrachloroethane or dichloroethane) at 50° C to 300° C, preferably at 100° C to 200° C The condensation (ii) gives compounds of formula [I] wherein A is a carbonyl group.

(iii) By reacting a compound of the formula:

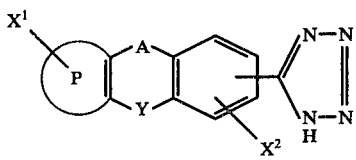

[Ia]

wherein each symbol is as defined above, with a compound of the formula:

R²—W      [IV]

wherein R² is as defined for R above, except that it may not represent a hydrogen atom, and W is a halogen atom (e.g. Cl, Br or I), a tolylsulfonyloxy group, a phenylsulfonyloxy group or a methylsulfonyloxy group.

The reaction is usually carried out in an inert solvent (e.g. dimethylformamide, dimethyl sulfoxide, water, ethanol, pyridine or toluene) at 0° C to 150° C for 2 to 4 hours, advantageously in the presence of a deacidifying agent (e.g. sodium carbonate, potassium carbonate, sodium hydroxide, sodium amide, sodium hydride, triethylamine or pyridine) at 50° C to 100° C.

The reaction (iii) gives compounds of formula [I] wherein R is other than a hydrogen atom.

The starting compounds of formula [II] can be produced, for example, by the method described in German Patent Publication Laid-Open No. 2,413,150 on Oct. 3, 1974, and the starting compounds of formula [III] can be produced, for example, by the route shown in the following reaction schema and preparation examples.

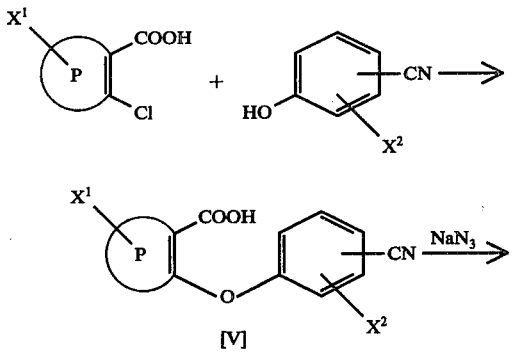

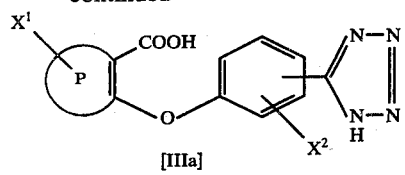

[IIIa]

Specific example of the preparation of [V]

To a solution of 6.9 g of metallic sodium in 90 ml of methanol are added 24 g of 2-chloronicotinic acid and 18 g of 4-hydroxybenzonitrile. The methanol is distilled off under reduced pressure, 60 ml of nitrobenzene is added, and the mixture is allowed to stand at 180° C to 190° C for 6 hours. After cooling, an aqueous potassium carbonate solution is added to the reaction mixture, and the whole mixture is filtered off. The aqueous layer is separated, washed with ethyl acetate and made acid with hydrochloric acid. The crystalline precipitate is recrystallized from aqueous ethanol to give 18 g of 2-(4-cyanophenoxy)nicotinic acid melting at 198° C to 200° C.

Specific example of the preparation of [IIIa] to be used in method (iii)

A mixture of 14.5 g of 2-(4-cyanophenoxy)nicotinic acid, 3.97 g of ammonium chloride, 4.96 g of sodium azide and 120 ml of dimethylformamide is allowed to stand at 100° C to 110° C for 24 hours. After cooling, the reaction mixture is filtered, and the filtrate is concentrated. To the residue is added a dilute hydrochloric acid, and the crystals are filtered off and recrystallized from methanol to give 5 g of 2-[4-(5-1H-tetrazolyl)-phenoxy]-nicotinic acid melting at 225° C to 230° C with decomposition.

The compounds of formula [I] wherein R is a hydrogen atom can be converted in a conventional manner into the corresponding metal salts (the metal being for example Na, K, Ca or Al); the compounds of formula [I] wherein R is a substituted or unsubstituted amino-alkyl group into the corresponding acid addition salts with various inorganic or organic acids such as hydrochloric, hydrobromic, sulfuric, oxalic, maleic and fumaric acid; and the compounds of formula [I] wherein R is a carboxyalkyl group into the corresponding metal salts mentioned above, the corresponding ammonium salts and the corresponding base addition salts (the base being for example triethylamine, diethylamine, morpholine or piperazine).

The compounds of formula [I] and pharmaceutically acceptable salts thereof have anti-allergic action as shown, for example, by the following tests; in which Compound A and B mean the following compounds.

Compound A: 7-(5-1H-tetrazolyl)-5-oxo-5H-[1]benzopyrano[2,3-b]pyridine,

Compound B: 9-chloro-7-(5-1H-tetrazolyl)-5-oxo-5-H-[1]benzopyrano[2,3-b]-pyridine.

Histamine release from the peritoneal cavity:

The method used was similar to that described by Hanahoe et al. (T.H.P. Hanahoe, A. Holliman, D. Gordon and W. Wieczorek, J. Pharm. Pharmac. 24, 666 (1972)). Groups of ten male Wistar rats (200–230 g) were injected intraperitoneally with 1 ml normal saline (0.9%) containing different amounts of test compound. A half minutes later they received an intraperitoneal injection of dextran (180 mg/kg, molecular weight about 250,000) or saline as vehicle control. Five minutes later the animals were killed, the peritoneal fluid was collected and centrifuged, and the supernatant was assayed fluorophotometrically for histamine. In this experimental method, disodium cromoglycate which is an inhibitor of reaginic anaphylaxis inhibits markedly the release of histamine. Therefore, Hanohoe et al. have suggested that dextran-induced histamine release may be initiated by a means similar to that of the immunological release of histamine. The percent inhibition was calculated using the following formula:

$$\text{Percent inhibition} = (1 - \frac{B - C}{A - C}) \times 100$$

A: histamine contents in saline-dextran-treated rats.
B: histamine contents in compound-dextran-treated rats.
C: histamine contents in vehicle-treated rats.

The $ED_{50}$, the dose required for 50% inhibition, was calculated from the dose-responsive curve.

Release of slow reacting substance of analphylaxis (SRS-A):

Guinea-pigs were sensitized with egg albumen, which was administered as a 10% solution, 100 mg both intraperitoneally and subcutaneously. Three to four weeks later the animals were killed by a blow on the head and the heart and lungs removed from the body and cleaned of blood. The lung tissue was dissected free from the heart, trachea and major bronchioles and then finely chopped. Portions of the lung tissue in 5 ml of Tyrode solution were preincubated with each test solution (50 μl) containing a test compound for 5 minutes at 37° C, to those were added 50 μl of egg albumen (100 μg/ml in a final concentration). The incubation mixture were further incubated for 15 minutes at 37° C. After centrifugation, the supernatant was assayed for SRS-A. The activity of SRS-A was assayed on the isolated guinea-pig ileum in the presence of atropine ($5 \times 10^{-8}$ g/ml) and pyribenzamine ($10^{-7}$ g/ml). The percent inhibition was calculated using the following formula:

Percent inhibition =
$$(1 - \frac{\text{SRS-A activity of agent-treated group}}{\text{SRS-A activity of control group}}) \times 100$$

The results are summarized in the following table.

| Compound | Histamine release (dextran i.p.) $ED_{50}$ mg/kg | SRS-A release μg/ml | % inhibition |
|---|---|---|---|
| Compound A | 0.001 | 0.01 | 25.2 |
| | | 0.1 | 35.3 |
| Compound B | 0.00025 | 0.01 | 19.0 |
| | | 0.1 | 22.6 |

The pharmaceutical composition can take the form of tablets, granules, powder or capsules, for oral administration, of injectable solution for subcutaneous or intramuscular administration, of aerosol inhalant for intranasal administration, or of cream, ointment or jelly for topical administration. The choice of carrier is determined by the preferred form of administration, the solubility of the compounds and standard pharmaceutical practice.

The following is an example of formulations when a compound of the invention is administered for pharmaceutical purposes: 50-mg capsules are prepared by encapsulating the following composition:

| | | |
|---|---|---|
| Compound of Example 1 | 50 | mg |
| Corn starch | 30 | |
| Lactose | 57.3 | |
| Calcium stearate | 0.7 | |
| Hydroxypropyl cellulose | 1 | |
| Finely powdered silica (sold under the registered Trade Mark "Aerosil") | 1 | |
| | 140 | mg |

50-mg tablets are prepared by tabletting the following composition:

| | |
|---|---|
| Compound of Example 1 | 50 mg |
| Lactose | 36 |
| Corn starch | 30 |
| Calcium stearate | 1 |
| Hydroxypropyl cellulose | 1 |
| Talc | 2 |
| | 120 mg |

The tablets may be sugar-coated in a conventional manner. A 1% aerosol inhalant is prepared according to the following recipe:

| | |
|---|---|
| Compound of Example 1 | 1% |
| Sorbiton trioleate | 0.1 |
| $Cl_2FC\text{-}CFCl_2$ (sold as Freon-113) | 13.9 |
| $CFCl_3$ (sold as Freon-11) | 19.5 |
| $CF_2Cl_2$ (sold as Freon-12) | 46 |
| $ClF_2C\text{-}CF_2Cl$ (sold as Freon-114) | 19.5 |
| | 100% |

("Freon" is a registered Trade Mark)

A 1% ointment is prepared from the following components:

| | |
|---|---|
| Compound of Example 1 | 1% |
| Distilled water | 35.3 |
| White petroleum | 40 |
| Cetanol | 18 |
| Sorbitan sesquioleate | 5 |
| Lauric acid ester of polyethylene glycol | 0.5 |
| Ethyl parahydroxybenzoate | 0.1 |
| Butyl parahydroxybenzoate | 0.1 |
| | 100% |

The recommended daily dose of compound of Example 1 lies in the range of 0.5 to 500 mg per human adult, depending upon the preparation form.

The present invention will be better understood from the following examples.

EXAMPLE 1

A mixture of 34 g of 5-oxo-5H-[1]benzopyrano[2,3-b]pyridine-7-carbonitrile, 460 ml of dimethylformamide, 10.5 g of ammonium chloride and 13.1 g of sodium azide is heated with stirring at 110° C to 120° C for 20 hours. After cooling, crystals are filtered off and added to a dilute hydrochloric acid, and the mixture is stirred. The crystals are filtered off, washed with water and recrystallized from dimethylformamide to give 29 g of 7-(5-1H-tetrazolyl)-5-oxo-5H-[1]benzopyrano[2,3-b]pyridine melting at above 300° C.

Elemental Analysis-Calcd. for $C_{13}H_7N_5O$: C-58.87, H-2.66, N-26.41; Found: C-58.65; L H-2.65; N-26.22.

EXAMPLE 2

A mixture of 4.8 g of 5-oxo-5H-[1]benzothiopyrano[2,3-b]pyridine-7-carbonitrile, 80 ml of dimethylformamide, 1.35 g. of ammonium chloride and 1.7 g of sodium azide is heated with stirring at 110° C to 120° C for 20 hours. After cooling, crystals are filtered off and added to a dilute hydrochloric acid, and the mixture is stirred. The crystals are filtered off, washed with water and recrystallized from dimethylformamide to give 3.8 g of 7-(5-1H-tetrazolyl)-5-oxo-5H-[1]benzothiopyrano[2,3-b]pyridine melting at above 300° C.

Elemental Analysis-Calcd. for $C_{13}H_7N_5OS$: C-55.52, H-2.51, N-24.90; Found: C-55.91, H-2.55, N-25.08.

EXAMPLE 3

A mixture of 5 g of 10-methyl-5-oxo-5H,10H-benzo[b][1,8]naphthyridine-7-carbonitrile, 50 ml of dimethylformamide, 1.45 g of ammonium chloride and 1.8 g of sodium azide is heated with stirring at 110° C to 120° C for 20 hours. After cooling, crystals are filtered off and added to a dilute hydrochloric acid, and the mixture is stirred. The crystals are filtered off, washed with water and recrystallized from dimethylformamide to give 4.3 g of 10-methyl-7-(5-1H-tetrazolyl)-5-oxo-5H,10H-benzo[b][1,8]naphthyridine melting at 321° C with decomposition.

EXAMPLE 4

A mixture of 0.5 g of 2-[4-(5-1H-tetrazolyl)phenoxy]-nicotinic acid and 5 ml of concentrated sulfuric acid is heated at 180° C for 2.5 hours, and then poured into ice water. The crystalline precipitate is filtered off, washed with water and with methanol and recrystallized from dimethylformamide to give 0.3 g of 7-(5-1H-tetrazolyl)-5-oxo-5H-[1]benzopyrano[2,3-b]pyridine melting at above 300° C.

EXAMPLE 5

A mixture of 1 g of 2-[2-methyl-4-(5-1H-tetrazolyl)-phenoxy]nicotinic acid and 10 ml of concentrated sulfuric acid is heated at 180° C for 2.5 hours, and then poured into ice water. The crystalline precipitate is filtered off, washed with water and with methanol and recrystallized from dimethylformamide to give 0.5 g of 9-methyl-7-(5-1H-tetrazolyl)-5-oxo-5H-[1]benzopyrano[2,3-b]pyridine melting at 290° C to 291° C with decomposition.

EXAMPLE 6

7-(5-1H-tetrazolyl)-5-oxo-5H-[1]benzopyrano[2,3-b]pyridine (3 g) is dissolved in 45 ml of dimethylformamide with heating at 100° C. To the solution is added 1.8 g of potassium carbonate, and the mixture is heated with stirring at 100° C for 20 minutes (crystals of potassium salt yield). After cooling to 60° C, 2 ml of methyl iodide is added to the mixture (the crystals of potassium salt gradually dissolve with a slight generation of heat). The mixture is allowed to stand at 60° C for 2 hours, and then poured into water. The crystalline precipitate is filtered off, washed with water and recrystallized from aqueous dimethylformamide to give 2.1 g of 7-(1-methyl-5-1H-tetrazolyl)-5-oxo-5H-[1]benzopyrano[2,3-b]pyridine melting at 248° C with decomposition.

EXAMPLE 7

7-(5-1H-tetrazolyl)-5-oxo-5H-[1]benzopyrano[2,3-b]pyridine (4 g) is dissolved in 60 ml of dimethylformamide with heating at 100° C. To the solution is added 2.4 g of potassium carbonate, and the mixture is heated at 100° C for 20 minutes (crystals of potassium salt yield). 2-Diethylaminoethyl chloride (2.6 g) is added dropwise to the mixture over a period of 20 minutes, and the whole mixture is allowed to stand at 90° C to 100° C for 2.5 hours and poured into water. A jelly-like substance produced is extracted with chloroform. The chloroform layer is washed with water, and the chloroform is distilled off. The crystalline residue is recrystalized from ethanol to give 2.8 g of 7-[1-(2-diethylaminoethyl)-5-1H-tetrazolyl]-5-oxo-5H-[1]benzopyrano[2,3-b]pyridine melting at 126° C to 128° C.

EXAMPLE 8

7-(5-1H-tetrazolyl)-5-oxo-5H-[1]benzopyrano[2,3-b]pyridine (5 g) is dissolved in a solution of 0.9 g of sodium hydroxide in 70 ml of water with heating. Ethanol (50 ml) is added to the solution, and the mixture is cooled. The crystalline precipitate is filtered off, washed with ethanol and recrystallized from aqueous ethanol to give 4.5 g of sodium salt of 7-(5-1H-tetrazolyl)-5-oxo-5H-[1]benzopyrano[2,3-b]pyridine melting at above 300° C.

Using the procedure set forth in the above examples, but substituting equivalent amounts of the appropriate starting materials, the following compounds are also produced:

1. 7-(5-1H-tetrazolyl)-5H-[1]benzopyrano[2,3-b]pyridine;
2. 7-(5-1H-tetrazolyl)-5,5-dimethyl-5H-[1]benzopyrano[2,3-b]pyridine, melting at 230°–240° C with decomposition;
3. 9-(5-1H-tetrazolyl)-5-oxo-5H-[1]benzopyrano[2,3-b]pyridine, melting at 275° C with decomposition;
4. 8-(5-1H-tetrazolyl)-10-oxo-10H-[1]benzopyrano[3,2-c]pyridine, melting at 317° C with decomposition;
5. 9-chloro-7-(5-1H-tetrazolyl)-5-oxo-5H-[1]benzopyrano[2,3-b]pyridine, melting at above 300° C;
6. 6-chloro-8-(5-1H-tetrazolyl)-10-oxo-10H-[1]benzopyrano[3,2-c]pyridine, melting at above 300° C;
7. 9-methoxy-7-(5-1H-tetrazolyl)-5-oxo-5H-[1]benzopyrano[2,3-b]pyridine;
8. 2-phenyl-7-(5-1H-tetrazolyl)-5-oxo-5H-[1]benzopyrano[2,3-b]pyridine, melting at above 300° C;
9. 2-(p-chlorophenyl)-7-(5-1H-tetrazolyl)-5-oxo-5H-[1]benzopyrano[2,3-b]pyridine, melting at above 300° C;
10. 7-(1-methyl-5-1H-tetrazolyl)-5-oxo-5H-[1]benzothiopyrano[2,3-b]-pyridine melting at 218°–220° C;
11. 7-(1-methyl-5-1H-tetrazolyl)-2-phenyl-5-oxo-5H-[1]benzopyrano[2,3-b]pyridine, melting at 287° C with decomposition;
12. 7-(1-isopropyl-5-1H-tetrazolyl)-5-oxo-5H-[1]benzopyrano[2,3-b]pyridine, melting at 195°–196° C;
13. 7-(1-vinyl-5-1H-tetrazolyl)-5-oxo-5H-[1]benzopyrano[2,3-b]pyridine, melting at 211°–212° C with decomposition;
14. 7-(1-allyl-5-1H-tetrazolyl)-5-oxo-5H-[1]benzopyrano[2,3-b]pyridine, melting at 200°–202° C;
15. 7-[1-(2-propynyl)-5-1H-tetrazolyl]-5-oxo-5H-[1]benzopyrano[2,3-b]-pyridine;
16. 7-[1-(2-hydroxyethyl)-5-1H-tetrazolyl]-5-oxo-5H-[1]benzopyrano[2,3-b]pyridine, melting at 199°–200° C;
17. 7-[1-(2-propoxyethyl)-5-1H-tetrazolyl]-5-oxo-5H-[1]benzopyrano[2,3-b]pyridine, melting at 151°–153° C;
18. 7-[1-(2-dimethylaminoethyl)-5-1H-tetrazolyl]-5-oxo-5H-[1]benzopyrano[2,3-b]pyridine, melting at 177°–179° C; 19. 7-(1-carboxymethyl-5-1H-tetrazolyl)-5-oxo-5H-[1]benzopyrano[2,3-b]pyridine; and 20. 7-(1-ethoxycarbonylmethyl-5-1H-tetrazolyl)-5-oxo-5H-[1]benzopyrano[2,3-b]pyridine, melting at 214° C with decomposition.

What is claimed is:

1. The compound 7-(5-1H-tetrazolyl-5-oxo-5H[1]benzopyrano[2,3-b]pyridine and the pharmaceutically acceptable salt thereof.

2. The compound 9-chloro-7-(5-1H-tetrazolyl)-5-oxo-5H-[1]benzopyrano[2,3-b]pyridine and the pharmaceutically acceptable salt thereof.

* * * * *